(12) United States Patent
Pohl et al.

(10) Patent No.: US 8,637,458 B2
(45) Date of Patent: Jan. 28, 2014

(54) INSULIN WITH A STABLE BASAL RELEASE PROFILE

(75) Inventors: Roderike Pohl, Sherman, CT (US);
Nandini Kashyap, Danbury, CT (US);
Robert Hauser, Columbia, MD (US);
Koray Ozhan, Milford, CT (US);
Solomon S. Steiner, Mount Kisco, NY (US)

(73) Assignee: Biodel Inc., Danbury, CT (US)

( * ) Notice: Subject to any disclaimer, the term of this patent is extended or adjusted under 35 U.S.C. 154(b) by 168 days.

(21) Appl. No.: 12/778,719

(22) Filed: May 12, 2010

(65) Prior Publication Data

US 2011/0281790 A1 Nov. 17, 2011

(51) Int. Cl.
*A61K 38/28* (2006.01)
*C07K 14/62* (2006.01)

(52) U.S. Cl.
USPC .......................................................... 514/5.9

(58) Field of Classification Search
None
See application file for complete search history.

(56) References Cited

U.S. PATENT DOCUMENTS

| | | | |
|---|---|---|---|
| 2,354,211 A | | 7/1944 | Lang |
| 2,882,203 A | * | 4/1959 | Petersen et al. ............... 514/6.4 |
| 3,102,077 A | | 8/1963 | Chirstensen |
| 4,960,702 A | * | 10/1990 | Rice et al. ..................... 435/226 |
| 5,070,186 A | * | 12/1991 | Joergensen ................... 530/304 |
| 6,852,694 B2 | | 2/2005 | Van Antwerp |
| 7,192,919 B2 | | 3/2007 | Tzannis |
| 2003/0026872 A1 | * | 2/2003 | Dake et al. ...................... 426/72 |
| 2004/0048783 A1 | | 3/2004 | Brunner-Schwarz |
| 2009/0082255 A1 | | 3/2009 | Brunner-Schwarz |
| 2009/0175840 A1 | | 7/2009 | Kashyap et al. |
| 2009/0312236 A1 | * | 12/2009 | Beals et al. ....................... 514/3 |
| 2009/0325860 A1 | | 12/2009 | Costantino |

FOREIGN PATENT DOCUMENTS

| | | |
|---|---|---|
| WO | WO 00/29013 | 5/2000 |
| WO | WO 03/002141 | 1/2003 |
| WO | 03020201 | 3/2003 |
| WO | WO 03/105888 | 12/2003 |
| WO | WO 2007/041481 | 4/2007 |
| WO | 2009089181 | 7/2009 |
| WO | 2010028055 | 3/2010 |

OTHER PUBLICATIONS

Hallas-Moller et al., Science 116: 394-398, 1952.*
Brange, et al., "Chemical stability of insulin 1: hydrolytic degradation during storage of pharmaceutical preparations", *Pharm. Res.*, 9:715-726 (1992).
Brange, et al., "Insulin Structure and stability", *Pharm Biotechnol.*, 5:315-50 (1993).
Dunn, "Zinc-ligand interactions modulate assembly and stability of the insulin hexamer", *Biometals*, 18(4):295-303 (2005).
Garber, "Premixed insulin analogues for the treatment of diabetes mellitus.", *Drugs*, 66(1):31-49 (2006).
Hagedorn, et al., "Protamine insulin", *JAMA*, 106:177-180 (1936).
Prabhu, et al. "A study of factors controlling dissolution kinetic of zinc complexed protein suspensions in various ionic species", *Int. J. Pharm.*, 217(1-2):71-78 (2001).
Guinn, et al., "Minimizing the aggregation of insulin solutions", *J. Pharmaceutical Sci.*, 72:1472-1473 (1983).
Rosenstock, et al., "Advancing insulin therapy in type 2 diabetes previously treated with glargine plus oral agents: prandial premixed (insulin lispro protamine suspension/lispro) versus basal/bolus (glargine/lispro) therapy.", *Diabetes Care*, 31(1):20-25 (2008).
Sanofi-Aventis, "Lantus(insulin glargine) injection solution", URL//:http://dailymed.nlm.nih.gov/dailymed/archives/fdaDrugInfo.cfm?archiveid=3517, retrieved on Sep. 12, 2011.
IUBMB Enzyme Nomenclature, EC 1.11.1.6,1 page, accessed Feb. 6, 2012 from www.chem.qmul.ac.uk/iubmb/emzyme/EC1/11/1/6.html, originated 1961, updated 1999.

* cited by examiner

*Primary Examiner* — Gyan Chandra
(74) *Attorney, Agent, or Firm* — Pabst Patent Group LLP

(57) ABSTRACT

A basal insulin formulation composed of insulin, preferably insulin glargine, injectable zinc and injectable iron compounds as precipitating and/or stabilizing agents has been developed for subcutaneous, intradermal or intramuscular administration. The formulation is designed to form a precipitate of insulin following injection, creating a slow releasing "basal insulin" over a period of 12 to 24 hours.

24 Claims, 2 Drawing Sheets

INSULIN WITH A STABLE BASAL RELEASE PROFILE

FIELD OF THE INVENTION

The present invention generally relates to formulations containing insulin in a formulation providing a more stable, longer extended release of insulin following administration.

BACKGROUND OF THE INVENTION

Glucose is a simple sugar used by all the cells of the body to produce energy and support life. Humans need a minimum level of glucose in their blood at all times to stay alive. The primary manner in which the body produces blood glucose is through the digestion of food. When a person is not getting sufficient glucose from food digestion, glucose is produced from stores in the tissue and released by the liver. The body's glucose levels are primarily regulated by insulin. Insulin is a peptide hormone that is naturally secreted by the pancreas. Insulin helps glucose enter the body's cells to provide a vital source of energy.

When a healthy individual begins a meal, the pancreas releases a natural spike of insulin called the first-phase insulin release. In addition to providing sufficient insulin to process the glucose entering the blood from digestion of the meal, the first-phase insulin release acts as a signal to the liver to stop making glucose while a meal is being digested. Because the liver is not producing glucose and there is sufficient insulin to process the glucose from digestion, the blood glucose levels of healthy individuals remain relatively constant and their blood glucose levels do not become too high.

Diabetes is a disease characterized by abnormally high levels of blood glucose and inadequate levels of insulin. There are two major types of diabetes—Type 1 and Type 2. In Type 1 diabetes, the body produces no insulin. In the early stages of Type 2 diabetes, although the pancreas produces insulin, either the body does not produce the insulin at the right time or the body's cells ignore the insulin, a condition known as insulin resistance.

Even before any other symptoms are present, one of the first effects of Type 2 diabetes is the loss of the meal-induced first-phase insulin release. In the absence of the first-phase insulin release, the liver will not receive its signal to stop making glucose. As a result, the liver will continue to produce glucose at a time when the body begins to produce new glucose through the digestion of the meal. As a result, the blood glucose level of patients with diabetes goes too high after eating, a condition known as hyperglycemia. Hyperglycemia causes glucose to attach unnaturally to certain proteins in the blood, interfering with the proteins' ability to perform their normal function of maintaining the integrity of the small blood vessels. With hyperglycemia occurring after each meal, the tiny blood vessels eventually break down and leak. The long-term adverse effects of hyperglycemia include blindness, loss of kidney function, nerve damage and loss of sensation and poor circulation in the periphery, potentially requiring amputation of the extremities.

Between two and three hours after a meal, an untreated diabetic's blood glucose becomes so elevated that the pancreas receives a signal to secrete an inappropriately large amount of insulin. In a patient with early Type 2 diabetes, the pancreas can still respond and secrete a large amount of insulin. However, this occurs at the time when digestion is almost over and blood glucose levels should begin to fall. This inordinately large amount of insulin has two detrimental effects. First, it puts an undue extreme demand on an already compromised pancreas, which may lead to its more rapid deterioration and eventually render the pancreas unable to produce insulin. Second, too much insulin after digestion leads to fat storage and weight gain, which may further exacerbate the disease condition.

Because patients with Type 1 diabetes produce no insulin, the primary treatment for Type 1 diabetes is daily intensive insulin therapy. The treatment of Type 2 diabetes typically starts with management of diet and exercise. Although helpful in the short-run, treatment through diet and exercise alone is not an effective long-term solution for the vast majority of patients with Type 2 diabetes. When diet and exercise are no longer sufficient, treatment commences with various non-insulin oral medications. These oral medications act by increasing the amount of insulin produced by the pancreas, by increasing the sensitivity of insulin-sensitive cells, by reducing the glucose output of the liver or by some combination of these mechanisms. These treatments are limited in their ability to manage the disease effectively and generally have significant side effects, such as weight gain and hypertension. Because of the limitations of non-insulin treatments, many patients with Type 2 diabetes progress over time and eventually require insulin therapy to support their metabolism.

Insulin therapy has been used for more than 80 years to treat diabetes. Intensive insulin therapy for diabetes involves providing a basal insulin, ideally present at a uniform level in the blood over a 24 hour period, and a bolus or meal time (prandial) insulin to cover the added carbohydrate load from digestion concomitant with each meal.

In 1936, Hans Christian Hagedorn and B. Norman Jensen discovered that the effects of injected insulin could be prolonged by the addition of protamine obtained from the "milt" or semen of river trout. The insulin was added to the protamine and the solution was brought to pH 7 for injection. In 1946, Nordisk Company was able to form crystals of protamine and insulin and marketed it in 1950 as NPH ("Neutral Protamine Hagedorn") insulin. NPH insulin has the advantage that it can be mixed with an insulin that has a faster onset to compliment its longer lasting action.

In the 1950's and 1960's high concentrations of zinc (greater than 2% zinc bound to amorphous insulin) were used to stabilize precipitated insulin, creating a prolonged insulin effect. These formulations created the lente, semi-lente and ultra lente formulations of long acting insulin, intended for basal use (U.S. Pat. No. 3,102,077 to Christensen; U.S. Pat. No. 2,882,203 to Petersen). However, due to the unpredictability of the insulin release profile, these basal formulations have gradually been replaced by formulations providing a more "peakless" profile.

Until very recently, and in many places today, basal insulin is usually provided by the administration of two daily doses of NPH insulin, separated by 12 hours. A patient eating three meals a day and using NPH insulin as the basal insulin requires five injections per day, one with each of three meals and two NPH insulin injections, one in the morning and the other at bedtime. To reduce the number of injections the patient must take, the morning dose of NPH insulin has been combined with a short acting insulin, (recombinant human insulin) or a rapid acting insulin analog, such as lispro. A typical combination is a 70% NPH to 30% rapid acting insulin analog mixture. As a result, the patient can reduce the number of injections from five per day to four per day. See, e.g., Garber, *Drugs,* 66(1):31-49 (2006).

More recently insulin glargine, (trade name LANTUS®) a "very long-acting" insulin analog has become available. It starts to lower blood glucose slowly after injection and keeps working for up to 24 hours, with a range of 14-26 hours, depending on the patient' individual needs. It differs from human insulin by having a glycine instead of asparagine at position 21 and two arginines added to the carboxy-terminus of the beta-chain. Insulin glargine is formulated at pH 4, where it is completely water soluble. After subcutaneous or intramuscular injection, the pH increases, causing the drug to precipitate, with just a small amount remaining soluble. This ensures that small amounts of LANTUS® are released into the body continuously, giving a nearly peakless profile. LANTUS® consists of insulin glargine dissolved in a clear aqueous fluid (100 IU, 3.6378 mg insulin glargine, 30 micrograms zinc, 2.7 mg m-cresol, 20 mg glycerol 85%, and water to 1 ml).

Rosenstock, et al. (Diabetes Care. 31(1):20-5 (2008)), reported that patients who took insulin glargine had a much lower risk of low blood glucose (hypoglycemia) than the patients who took NPH insulin because of the predictable insulin release. Insulin spikes in the plasma can lead to hypoglycemia. During the day hypoglycemia can result in loss of mental acuity, confusion, increased heart rate, hunger, sweating and faintness. At very low glucose levels, hypoglycemia can result in loss of consciousness, coma and even death. While sleeping, these symptoms are not evident, so the patient is not aware of the need to ingest food to increase the glucose levels in the blood. Therefore, the predictability of insulin release overnight is critical. According to the American Diabetes Association (ADA), insulin-using diabetic patients have on average 1.2 serious hypoglycemic events per year, many requiring hospital emergency room visits by the patients. Therefore, a reliable slow releasing insulin formulation is extremely important for treatment of diabetes.

It is therefore an object of the present invention to provide a stable basal insulin with extended release properties.

SUMMARY OF THE INVENTION

The basal insulin formulation for subcutaneous or intramuscular injection, contains insulin glargine (LANTUS®), a zinc compound, and an iron compound, in amounts effective to stabilize and enhance release. The clear solution, once injected, precipitates into a sustained releasing basal insulin as the bodily fluids at neutral pH (7-7.4) mix with the insulin solution post injection. The zinc chloride and iron dextran further enhance precipitation of the insulin particles, making them less soluble. These "enhanced" precipitated insulin particles persist longer in the subcutaneous tissue, resulting in a sustained release of insulin over a controlled period of time, for example, 24 hours, as depicted in FIG. 1 in miniature diabetic swine. A precipitation enhancing agent such as zinc chloride in combination with an iron compound such as iron dextran or ferrous gluconate is used to promote precipitation post injection. The iron compound further enhances stability and duration of release, in the preferred embodiment by about 25%. The release profiles can be varied by adjusting the pH as well as the amount and ratio of excipients.

In other embodiments, using human recombinant, bovine or porcine insulin, or insulin analogs, the formulation may also contain buffering components that sustain the pH around the isoelectric point of approximately pH 5.5, enhancing the precipitation of insulin into particles post injection. The buffering agents may be used alone or in conjunction with charged amino acids such as arginine to reduce the solubility at physiological pH. The zinc and iron compounds also stabilize and enhance release of these formulations.

DETAILED DESCRIPTION OF THE INVENTION

I. Definitions

Figure 1:
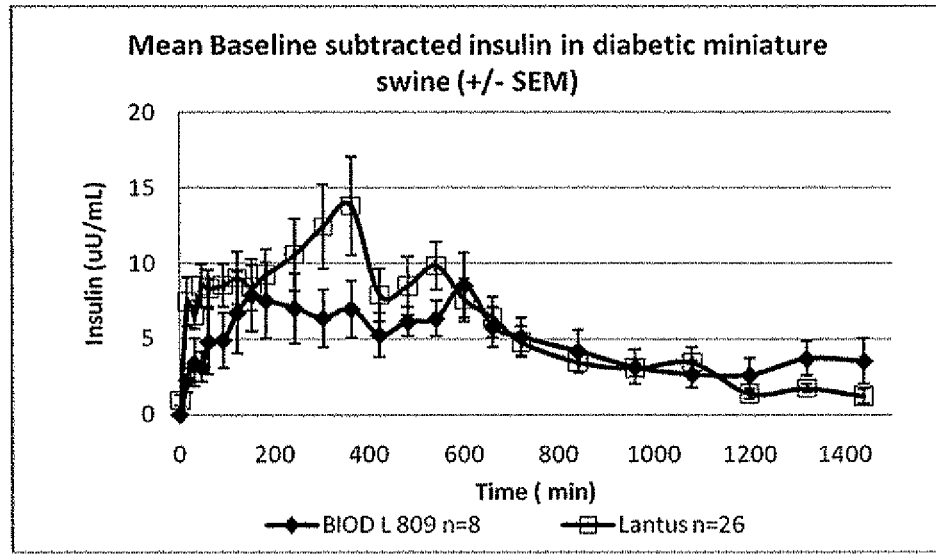
FIG. 1 is a graph of mean baseline subtracted insulin concentrations in miniature swine following injection with either Lantus® (open squares, n=26) or BIOD L 809 (solid diamonds, n=8) over time in minutes. BIOD 809 is insulin glargine in combination with 1 mg/ml iron dextran and 2 mg/ml $ZnCl_2$.

As used herein, "a less soluble insulin" refers to an insulin or insulin analog that is less soluble than human recombinant insulin in extracellular fluid, such as Earle's balanced salt solution E2888 (Sigma Aldrich) at physiological pH (6.2-7.4) and body temperature (e.g. 37° C.).

As used herein, "insulin" refers to human or non-human, recombinant, purified or synthetic insulin or insulin analogues, unless otherwise specified.

As used herein, "human insulin" is the human peptide hormone secreted by the pancreas, whether isolated from a natural source or made by genetically altered microorganisms.

As used herein, "non-human insulin" is insulin but from a non-human animal source such as a pig or cow. Bovine and porcine insulins differ in several amino acids from human insulin, but are bioactive in humans.

As used herein, an "insulin analogue" is a modified insulin, different from the insulin secreted by the pancreas, but still available to the body for performing the same or similar action as natural insulin. Through genetic engineering of the underlying DNA, the amino acid sequence of insulin can be changed to alter its absorption, distribution, metabolism, and excretion (ADME) characteristics. Examples include insulin lispro, insulin glargine, insulin aspart, insulin glulisine, and insulin detemir. The insulin can also be modified chemically, for example, by acetylation.

As used herein, "human insulin analogues" are altered human insulins which are able to perform an action similar to human insulin.

As used herein, a "precipitating agent" refers to a chemical that causes or enhances the formation of an insulin precipitate, "seeds" an insulin precipitate, modifies the solubility of insulin at physiological pH, or stabilizes the pH of the insulin at the isoelectric point to induce or maintain precipitation.

As used herein, a "buffer" is a chemical agent able to absorb a certain quantity of acid or base without undergoing a strong variation in pH.

As used herein, an "insulin stabilizing agent" is an agent that physically and chemically stabilizes the insulin by preventing the formation of breakdown products reducing the potency of the insulin. Examples include zinc at low concentrations (50 µg/mL or lower concentrations), while zinc at high concentrations is used as a precipitating agent.

As used herein, a "precipitate enhancing agent" refers to agents that enhance the stability of precipitated insulin particles. Zinc is both an insulin stabilizing agent and a precipitate stabilizing agent.

As used herein, "a prandial insulin" refers to an insulin or insulin formulation that provides a short term rapid release insulin and delivers an effective amount of insulin to a patient to manage the patient's blood glucose fluctuations following a meal. Typical prandial insulins include rapid-acting insulin analogs, which have a pharmacokinetic profile that closely resembles endogenous insulin.

As used herein, "a basal insulin" refers to an insulin or insulin formulation that provides levels of insulin over a period of time after administration of about 12 to 24 hours effective amount of insulin to manage the patient's normal daily blood glucose fluctuations in the absence of a meal.

As used herein, "a basal release profile" refers to the amount and rate of release of insulin from the formulation into a patient's systemic circulation. In a graph of the patient's mean plasma insulin levels over time, a basal release profile generally has a minimal peak (often referred to as "a peakless profile") and slowly and continuously releases insulin for a prolonged period of time, such as twelve to twenty-four hours following administration. One example of a formulation with a basal release profile is LANTUS®.

As used herein, a "suspending agent" refers to a substance added to retard the sedimentation of suspended particles in liquids.

As used herein, an "excipient" refers to an inactive substance used as a carrier, to control release rate, adjust isotonicity or aid the process by which a product is manufactured. In such cases, the active substance is dissolved or mixed with an excipient.

As used herein, a "pharmaceutically acceptable carrier" refers to a non-toxic, inert solid, semi-solid or liquid that is not pharmaceutically active, which is mixed with the pharmaceutically active agent. Remington's Pharmaceutical Sciences Ed. by Gennaro, Mack Publishing, Easton, Pa., 1995 discloses various carriers used in formulating pharmaceutical compositions and known techniques for the preparation thereof.

II. Composition

The compositions contain insulin and excipients for injection, including zinc and iron compounds. In the preferred embodiment, the formulation includes insulin glargine and excipients, is suitable for subcutaneous administration, and the insulin is slowly released into the systemic circulation.

In one embodiment, regular human insulin is administered as a clear solution of insulin, in a concentrate of between 10 to 500 Units, in combination with a buffer such as a citrate or acetate (approximately pH 4), with an excess of zinc ions to maintain the insulin as a stable hexamer and enhance precipitation and iron dextran or other iron containing compound to further sustain release. This is injected into the subcutaneous tissue or muscle. The tissue has a pH of about pH 6.8-7.2. As the pH of the injected insulin rises due to diffusion of the surrounding higher pH fluids, the insulin passes through its isoelectric point of about 5.5, creating a microprecipitate at the site of the injection. The buffer slows the progression to a pH of 7. The precipitated insulin then dissolves at a slow rate, and is absorbed through the capillaries, creating a basal systemic insulin profile. As demonstrated by the examples, the addition of an injectable iron compound extends the s release.

A. Insulin

In the preferred embodiment, the formulation contains insulin glargine. Alternatively, the insulin can be recombinant or purified from a natural source. The insulin can be human or non-human, such as porcine or bovine. The insulin may also be an insulin analogue which may be based on the amino acid sequence of human insulin but having one or more amino acids differences, or a chemically modified insulin or other insulin analog. An "insulin analogue" is a modified insulin, different from the insulin secreted by the pancreas, but still available to the body for performing the same or similar action as natural insulin. Through genetic engineering of the underlying DNA, the amino acid sequence of insulin can be changed to alter its absorption, distribution, metabolism, and excretion (ADME) characteristics. Examples include insulin lispro, insulin glargine, insulin aspart, insulin glulisine, and insulin detemir. The insulin can also be modified chemically, for example, by acetylation. The "human insulin analogues" are altered human insulins which are able to perform an action similar to human insulin.

B. Insulin Stabilizing Agents

Stabilizing agents are included in the formulation specifically to stabilize insulin as a hexamer in solution or reduce formation of B21 desamido which forms at pH 4 or other degradation products which form at neutral pH or above. An example is zinc chloride at a concentration of 50 mg/mL or lower.

C. Precipitating Agents

Precipitating agents are added to enhance the formation of the insulin precipitate by either hastening the precipitate formation, and/or stabilizing the precipitate by reducing its solubility. These may be buffering agents, solubility modifying agents, precipitation seeding agents, or precipitation enhancing agents.

As the pH is increased from pH 4 towards physiological pH (7-7.5, typically 7.2-7.4), regular human insulin transitions through its isoelectric point (pI) of about 5.5. The amount of precipitate may be increased or form of the precipitate may be altered by increasing the residence time of the insulin at approximately its pI. This may be achieved by adding a buffering agent to the insulin formulation that is specifically selected for sufficient buffering capacity in the range of insulin's pI. Buffering agents include acetate, citrate, phosphate, carbonate, and barbital. Preferred buffering agents are GRAS ingredients.

In the preferred embodiment precipitation enhancing agents are added to form or stabilize an insulin precipitate. Precipitation agents include various forms of zinc, calcium, magnesium, manganese, iron, copper, and other divalent ions used at non-toxic levels (range 0.1-10 mg/ml, preferably 2.5 mg). Preferred iron agents include iron dextran, ferrous gluconate, ferrous sulfate and other injectable iron agents.

In one embodiment used with regular human insulin, a pH buffer, sodium acetate is used at a concentration ranging from 0.2 to 20 mg/mL, preferably from 1 to 10 mg/mL, most preferably 6 mg/mL, to precipitate the insulin. In another embodiment containing only a pH buffer where the insulin is present at a pH of about 8 as a clear solution and which forms a precipitate as the pH is dropped from 8 to 7 towards physiological pH, agents such as sodium phosphate or sodium citrate may be added to help form or stabilize the precipitate as it forms.

In a third embodiment using regular human insulin, a charged molecule modifies the solubility of insulin at physiological pH. Examples of charged molecules (or solubility modifying agents) include amino acids such as arginine, histidine, lysine. A representative concentration of histidine ranges from 0.005 to 10 mg/mL, preferably from 0.5 to 2 mg/ml. A representative concentration of Arginine ranges from 0.005 to 10 mg/mL, preferably ranges from 0.25 to 2 mg/mL.

Precipitation "seeding" agents may be a solid nanoparticle or a molecule that precipitates at or near the pI of the insulin, thereby acting as a nucleation site for the insulin. Examples of nanoparticles include $Au_{12}$ (present in the formulation in a concentration range from 24 to 2400 ng/ml, preferably 240 ng/ml) and $C_{60}$ (present in the formulation in a concentration range from 75 to 7500 ng/ml, preferably 750 ng/mL). An example of a molecule that precipitates near the pI of insulin is cysteine with a pI of 5.0. An appropriate concentration of cysteine in the formulation ranges from 1.2 to 120 nM, and preferably is 12 nM.

These precipitation agents may be used individually or combined to modify the pharmacokinetics of insulin precipitation and solubilization following injection. Typically these precipitation agents are added so that all of the insulin is solubilized within 8 to 24 hours following administration. The formulation is designed to create the best conditions for precipitation post injection, leading to a stable micro-precipitate. The choice of agents is dependent on the intended duration of the formulation (e.g. typically the formulation is intended to release insulin for 8 to 24 hours following injection, preferably for 12 to 24 hours following injection) allowing the profile to be catered to individual patient's needs.

One of the benefits of the formulations is that the amount of precipitate and release rate following administration can be adjusted through the selection and amount of excipients such as the zinc, iron and the pH buffer and/or amino acid. The insulin formulation can be provided in different compositions so that the physician can adjust the rate of release. These will have different release rates by a few hours, and can be labeled "short", "medium" and "long". A physician can try different formulations and test blood glucose levels to determine which is best for that patient.

D. Other Excipients and Carriers

The formulations are administered by injection, preferably subcutaneous injection. The insulin is preferably in combination with pharmaceutically acceptable carriers such as sterile water or saline. Suitable diluents include, but are not limited to, water, buffered aqueous solutions, dilute acids, vegetable or inert oils for injection, organic hydrophilic diluents, such as monovalent alcohols, and low molecular weight glycols and polyols (e.g. propylene glycol, polypropylene glycol, glycerol, and butylene glycol). Remington's Pharmaceutical Sciences Ed. by Gennaro, Mack Publishing, Easton, Pa., 1995 discloses various carriers used in formulating pharmaceutical compositions and known techniques for the preparation thereof.

The diluent typically contains one or more excipients. Examples of excipients in a typical diluent for an injectable formulation include glycols, salts, preservatives, and optionally a buffering agent. In the preferred embodiment, the diluent contains saline. In the preferred embodiments, no excipients other than pH buffers, charged molecules and/or precipitating enhancers or stabilizers are added, although salts to make a solution isotonic, acid or base to adjust pH, colorants, and/or preservatives may be added.

In one embodiment, the combined insulin composition has a pH of about 3.5 to about 5.0, below the isoelectric point of the insulin or sufficiently above it to form a clear solution. Suitable pH modifying agents include, but are not limited to, sodium hydroxide, citric acid, hydrochloric acid, acetic acid, phosphoric acid, succinic acid, sodium hydroxide, potassium hydroxide, ammonium hydroxide, magnesium oxide, calcium hydroxide, calcium carbonate, magnesium carbonate, magnesium aluminum silicates, malic acid, potassium citrate, sodium citrate, sodium phosphate, lactic acid, gluconic acid, tartaric acid, 1,2,3,4-butane tetracarboxylic acid, fumaric acid, diethanolamine, monoethanolamine, sodium carbonate, sodium bicarbonate, triethanolamine, and combinations thereof.

Preservatives can be used to prevent the growth of fungi and other microorganisms. Suitable preservatives include, but are not limited to, benzoic acid, butylparaben, ethyl paraben, methyl paraben, propylparaben, sodium benzoate, sodium propionate, benzalkonium chloride, benzethonium chloride, benzyl alcohol, cetypyridinium chloride, chlorobutanol, phenol, phenylethyl alcohol, m-cresol, thimerosal, polysorbate 20 and combinations thereof.

III. Methods of Making the Formulations

In the preferred embodiment, the insulin formulation is made by combining all constituents into the diluent, and adjusting to a final pH to make a clear solution (pH approximately 4 or 8). The solution is sterile filtered and filled in a vial suitable for multiple injection dosing.

Alternatively, the insulin is provided in a kit containing one vial of insulin in lyophilized form and another vial to resuspend the insulin. The excipients may be present in one or both vials, as appropriate to adjust pH, and stabilize and buffer the formulation.

IV. Methods of Using the Formulations

The formulations may be administered subcutaneously, intradermally or intramuscularly by injection. The formulation is designed to produce a basal profile of insulin following administration. Doses are administered once or twice a day, titered to each patient's individual requirements, based on glucose measurements and the patient's history. The typical dose of basal insulin is in the range of 0.3 U/kg/day, in a range of four to 500 units, although severe diabetics can be dosed as much as 60 Units.

The present invention will be further understood by reference to the following non-limiting examples.

EXAMPLES

Example 1

Excipients to Increase Duration of Release of Basal Insulin

Studies were conducted to determine which insulin glargine formulations would last longer post injection, with a "peakless" release profile.

Materials and Methods

Test formulations using commercial Lantus® were made by adding excipients to 1 mL of a clear pH 4 Lantus® solution. Excipients were: zinc chloride, phenylalanine, ferrous sulfate, iron dextran, and ferrous gluconate. The relative amounts are shown in Table 1.

The pH of the solution was then adjusted to 7 using a small quantity of 1N NaOH, which artificially induced the microprecipitate normally found post injection when the insulin is exposed to physiological pH. This precipitate was then diluted 240 fold in phosphate buffered saline solution and stirred for one minute at 37° C. The suspension (diluent and precipitate) was transferred into a centrifuge tube and spun for 6 minutes at 6000 rpm to pellet the suspended material. Supernatants were analyzed by HPLC for insulin content. Results are expressed in % total insulin in the supernatant (insulin found in supernatant/total insulin in tube*100).

The effect of the amount of zinc chloride and iron compound, either iron dextran or ferrous gluconate, on the amount of insulin in the supernatant was then determined. The amounts and relative amount of insulin in the supernatants was then determined.

Results

Results in Table 1 show that Lantus® without additional excipients has 90% of the microprecipate dissolved. Adding zinc chloride or an iron compound, either iron dextran or ferrous gluconate, decreases the amount of insulin in the supernatant. Iron compound in combination with zinc chloride is most effective in decreasing the amount of soluble insulin. Increasing the zinc chloride, for a total of 2 mg zinc chloride/mL and 1 mg iron dextran/mL, further decreased the amount of insulin in the supernatant (Table 3), although increasing the iron compound did not further decrease the amount of soluble insulin.

TABLE 1

Combinations of Excipients added to Lantus®

| Formulations | Zinc Chloride | Phenyl alanine | Ferrous Sulfate | Iron dextran | Ferrous gluconate | % insulin in supernatant |
|---|---|---|---|---|---|---|
| 1 | 1 | 0.5 | — | — | — | 73.32 |
| 2 | 0 | 0.5 | — | — | — | 77.10 |
| 3 | 1 | 2 | — | — | — | 62.82 |
| 4 | 0 | 2 | — | — | — | 83.53 |
| 5 | 1 | — | 1 | — | — | 62.91 |
| 6 | 0 | — | 1 | — | — | 72.44 |
| 7 | 1 | — | — | 1 | — | 54.91 |
| 8 | 0 | — | — | 1 | — | 82.02 |
| 9 | 1 | — | — | — | 1 | 58.24 |
| 10 | 0 | — | — | — | 1 | 76.36 |
| Lantus + 1 mg/ml ZnCl$_2$ | 1 | — | — | — | — | 62.57 |
| Lantus | 0 | — | — | — | — | 90.00 |

TABLE 2

Percent Insulin in Supernatant for Different Formulations

| Formulations | % insulin in supernatant |
|---|---|
| Lantus ® | 90.00 |
| Lantus ® + 1 ZnCl$_2$ | 62.57 |
| Lantus ® + 1 ZnCl$_2$ + 1 mg/ml ferrous gluconate | 59.87 |
| Lantus ® + 1 ZnCl$_2$ + 2 mg/ml ferrous gluconate | 63.81 |
| Lantus ® + 1 ZnCl$_2$ + 4 mg/ml ferrous gluconate | 61.95 |
| Lantus ® + 1 ZnCl$_2$ + 1 mg/ml iron dextran | 54.91 |
| Lantus ® + 1 ZnCl$_2$ + 2 mg/ml iron dextran | 57.75 |
| Lantus ® + 1 ZnCl$_2$ + 4 mg/ml iron dextran | 58.65 |

TABLE 3

Dosage Optimization for ZnCl$_2$ and Iron Dextran

| ZnCl$_2$ (mg/mL) | Iron Dextran (mg/mL) | % insulin in supernatant |
|---|---|---|
| 0 | 0 | 90.00 |
| 1 | 0 | 62.57 |
| 0 | 1 | 87.74 |
| 2 | 0 | 56.67 |
| 0 | 2 | 88.99 |
| 2 | 1 | 52.79 |

Example 2

Lantus® with ZnCl$_2$ and Iron Dextran in Diabetic Miniature Swine

Based on the results in Example 1, the insulin glargine formulation combining 2 mg zinc chloride/mL and 1 mg iron dextran/mL was administered to diabetic miniature swine.

Materials and Methods

BIOD L 809 is a blend of 2 mg/mL zinc chloride with 1 mg/mL iron dextran, added to Lantus®. The swine were fed the day prior to the study and given their typical porcine insulin injection. Baseline glucose levels were taken the morning of the study. At time=0 the pigs were given a shot of BIOD L809 (0.45 U/kg) and fed their morning meal. A second meal was given at 480 min. and plasma samples were taken over a 24 hour period (n=8). The Lantus® control is a compilation of 26 swine+/−SEM for comparison.

Glucose and insulin data obtained from the plasma samples provided PK and PD graphic information.

Results

Figure 2:
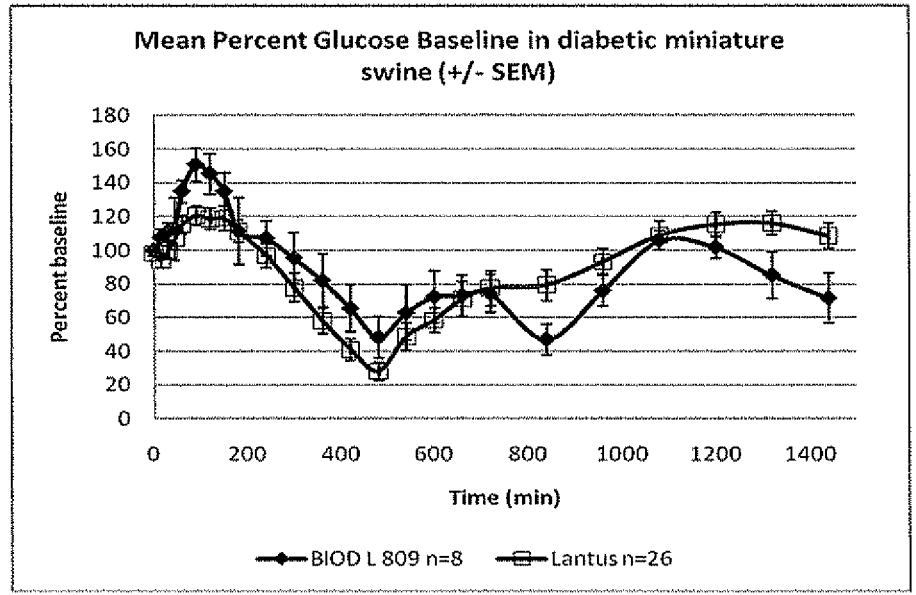
FIG. 2 is a graph of mean percent glucose lowering in miniature swine following injection with either Lantus® (open squares, n=26) or BIOD L 809 (solid diamonds, n=8) over time in minutes.
Figure 3:
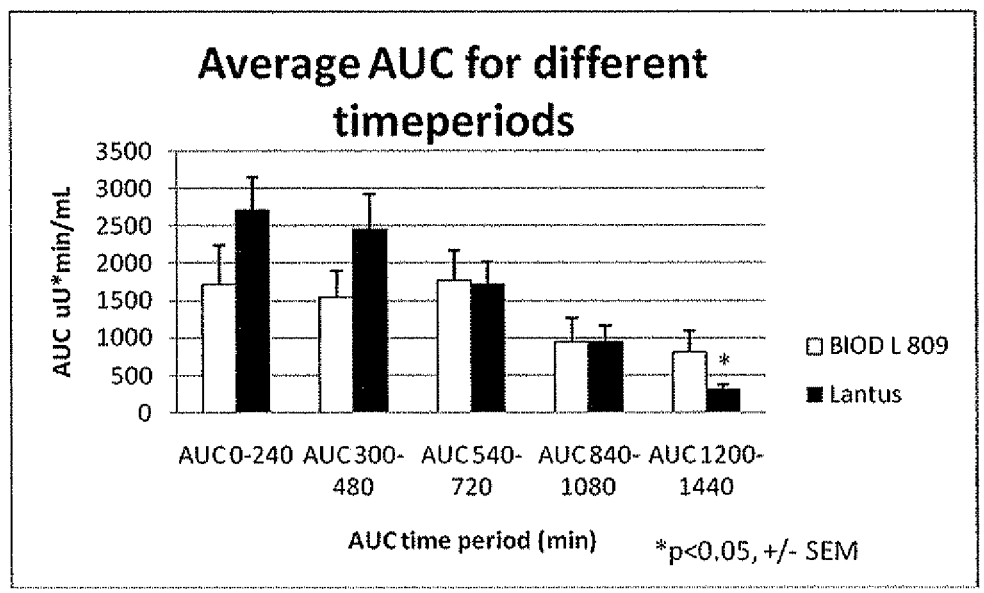
FIG. 3 is a bar graph of AUC calculated for time periods covering 24 hours of the data shown in FIGS. 1 and 2. Lantus=black, BIOD L 809=white.

The results are shown in FIGS. 2 and 3 and Table 4. The data show that BIOD L 809 has a smoother, less peaked insulin profile in the swine, which extends the full 24 hours. The percent glucose lowering shows the insulin is slowly released over time, and continues to have an effect beyond the second feeding of the swine. The insulin has returned to baseline at 1080 to 1200 min, clearly demonstrated by both the insulin and glucose profiles. The duration of action was determined as the time required to return to glucose baseline. BIOD L-809 had a significantly longer duration than Lantus®. The average percent blood glucose lowering was also calculated from the mean values, showing BIOD L809 had an average percent glucose that was lower than Lantus® in the second 12 hours post injection.

FIG. 3 is a bar graph of AUC calculated for time periods covering 24 hours. The data clearly demonstrates that BIOD L-809 provides a much more uniform level of insulin over time than the available Lantus® formulation.

Equivalent results were obtained with 0.5 ZnCl and 0.5 iron dextran.

TABLE 4

Duration of Release and Average Percent Glucose

|  | duration (min) | average percent blood glucose 720-1440 (min.) |
|---|---|---|
| Lantus | 1050 ± 55* | 99 ± 6.2 |
| BIOD L-809 | 1328 ± 85* | 80 ± 7.5 |

*p < 0.05

Unless defined otherwise, all technical and scientific terms used herein have the same meanings as commonly understood by one of skill in the art to which the disclosed invention belongs. Publications cited herein and the materials for which they are cited are specifically incorporated by reference.

Modifications and variations of the methods and materials described herein will be obvious to those skilled in the art from the foregoing description and are intended to be encompassed by the following claims.

We claim:

1. A basal insulin formulation comprising
   insulin or a modified insulin,
   with an injectable zinc compound and an injectable precipitation enhancing compound in an effective amount to precipitate the insulin and prolong release of solubilized insulin following injection, wherein precipitation of insulin is enhanced in the formulation comprising zinc and the precipitation enhancing compound as compared to the precipitation of insulin in the presence of the zinc or precipitation enhancing compound, wherein the precipitation enhancing agent contains an ion selected from the group consisting of, calcium, magnesium, manganese, iron, and copper, used at non-toxic levels, and is in a concentration between 0.1 to 10 mg precipitation enhancing agent/ml of basal insulin formulation.

2. The formulation of claim 1, wherein the zinc compound is selected from the group consisting of zinc acetate, zinc oxide, zinc citrate, zinc carbonate, zinc sulfate, and zinc chloride.

3. The formulation of claim 1, comprising zinc chloride in a concentration between 2 and 3 mg/mL.

4. The formulation of claim 3, comprising an iron compound selected from the group consisting of iron dextran, ferrous gluconate, ferrous sulfate and other injectable iron agents.

5. The formulation of claim 4 wherein the formulation comprises sodium acetate in a concentration between 0.2 and 20 mg/mL.

6. The formulation of claim 1, comprising an iron compound.

7. The formulation of claim 6, wherein the iron compound is selected from the group consisting of iron dextran, ferrous gluconate, ferrous sulfate and other injectable iron agents.

8. The formulation of claim 6, comprising insulin glargine and zinc chloride.

9. The formulation of claim 1, comprising recombinant human insulin further comprising a buffering agent selected from the group consisting of acetate, citrate, phosphate, carbonate, and barbital.

10. The formulation of claim 9, wherein the buffering agent is in a concentration between 1 and 10 mg/mL.

11. The formulation of claim 10, wherein the buffering agent is in a concentration between 5 and 6 mg/mL.

12. The formulation of claim 1, further comprising a solubility modifying agent selected from the group consisting of arginine, histidine, and lysine.

13. The formulation of claim 12 comprising arginine in a concentration between 0.005 and 10 mg/mL.

14. A method of providing a basal insulin to an individual in need thereof comprising administering the formulation of claim 13.

15. The method of claim 14, wherein the formulation is provided in two containers, wherein the insulin or modified insulin is provided in a first container as a lyophilized powder which is reconstituted at the time of administration and the arginine, injectable compound and injectable precipitation enhancing compound are present in one or both the containers.

16. The method of claim 15, wherein the contents of the two containers are mixed to form a clear solution prior to administration.

17. The formulation of claim 1, comprising at least one pH modifying agent selected from the group consisting of sodium hydroxide, citric acid, hydrochloric acid, acetic acid, phosphoric acid, succinic acid, sodium hydroxide, potassium hydroxide, ammonium hydroxide, magnesium oxide, calcium hydroxide, calcium carbonate, magnesium carbonate, magnesium aluminum silicates, malic acid, potassium citrate, sodium citrate, sodium phosphate, lactic acid, gluconic acid, tartaric acid, 1,2,3,4-butane tetracarboxylic acid, fumaric acid, diethanolamine, monoethanolamine, sodium carbonate, sodium bicarbonate, triethanolamine, and combinations thereof.

18. The formulation of claim 1, containing a preservative.

19. The formulation of claim 1, provided in a kit consisting of two or more containers which are mixed at the time of administration to form an insulin solution at the time of injection.

20. The formulation of claim 1, providing a basal effective amount of insulin for a period of 12 to 24 hours following administered by subcutaneous, intramuscular, or intradermal injection.

21. The formulation of claim 1, providing a insulin basal release profile for a short, medium or long duration, wherein the duration is 12 to 16 hours, 16 to 20, or 20 to 24 hours.

22. The formulation of claim 1, in the form of a clear solution which forms a precipitate at physiological pH.

23. A basal insulin formulation comprising
an insulin analog with an injectable zinc compound and an injectable precipitation enhancing compound in an effective amount to precipitate the insulin and prolong release of solubilized insulin following injection, wherein precipitation of insulin is enhanced in the formulation comprising zinc and the precipitation enhancing compound as compared to the precipitation of insulin in the presence of the zinc or precipitation enhancing compound, wherein the precipitation enhancing agent contains an ion selected from the group consisting of, calcium, magnesium, manganese, iron, and copper, used at non-toxic levels, and is in a concentration between 0.1 to 10 mg precipitation enhancing agent/ml of basal insulin formulation.

24. The formulation of claim 23, comprising insulin glargine.

* * * * *